United States Patent [19]
Oh et al.

[11] Patent Number: 5,100,416
[45] Date of Patent: Mar. 31, 1992

[54] LIGATING CLIP APPLYING INSTRUMENT

[75] Inventors: Seik Oh; Ray McKinney, Jr., both of Raleigh, N.C.

[73] Assignee: Edward Weck Incorporated, Princeton, N.J.

[21] Appl. No.: 587,928

[22] Filed: Sep. 24, 1990

Related U.S. Application Data

[60] Division of Ser. No. 422,464, Oct. 17, 1989, Pat. No. 5,062,846, which is a continuation-in-part of Ser. No. 329,453, Mar. 28, 1989, abandoned, which is a division of Ser. No. 206,143, Jun. 13, 1988, Pat. No. 4,834,096, which is a continuation-in-part of Ser. No. 112,599, Oct. 26, 1987, abandoned.

[51] Int. Cl.$^5$ .............................................. A61B 17/00
[52] U.S. Cl. ...................................... 606/139; 606/142
[58] Field of Search ................... 606/139, 142; 227/901

[56] References Cited

U.S. PATENT DOCUMENTS

| | | | |
|---|---|---|---|
| 3,631,707 | 1/1972 | Miller | 606/142 |
| 4,446,865 | 5/1984 | Jewusiak | 606/142 |

FOREIGN PATENT DOCUMENTS

| | | | |
|---|---|---|---|
| 2069848 | 9/1981 | United Kingdom | 606/142 |

*Primary Examiner*—Stephen C. Pellegrino
*Assistant Examiner*—Gary Jackson
*Attorney, Agent, or Firm*—Gene Warzecha

[57] ABSTRACT

A polymeric, surgical clip having first and second curved leg members joined at their proximal end by a reduced thickness hinge portion and movable from an open position to a closed position for clamping a vessel between curved opposing inner surfaces which are substantially parallel when the clip is closed. The first leg member has a concave inner surface and a hook portion at its distal end curved toward the second leg member. The clip includes a sharp distal tip on the end of the hook portion and a sharp pointed penetrating member on the outer surface of the distal end of the hook portion. The distal end of the second leg has a longitudinal groove through which the sharp pointed penetrating member and then the sharp distal tip passes when the legs are closed. The second leg member further comprises a pair of sharp penetrating member attached to each side of the distal end on either side of the groove. These cooperate with the penetrating member of the first leg and sharp distal tip to cut tissue attached to the vessel to be clamped. A ligating clip applying instrument for applying the clip has a pair of handles pivoted about a hinge point and extends beyond the hinge point to form a pair of clip closing jaws equipped with means for engaging bosses located on the sides of the first and second leg members.

7 Claims, 6 Drawing Sheets

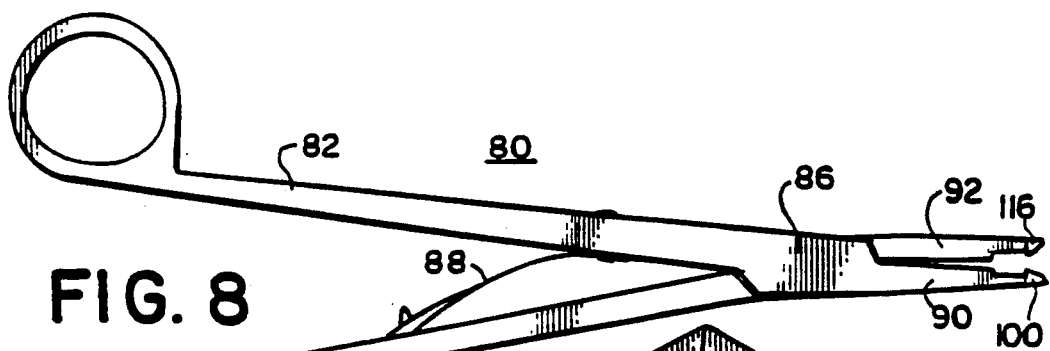
FIG. 8
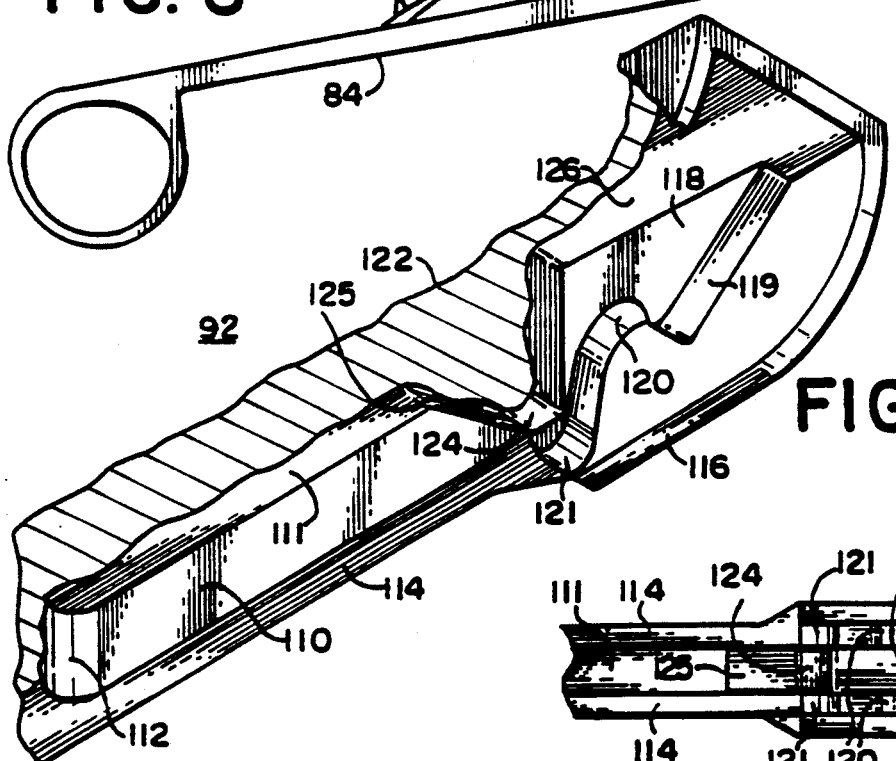
FIG. 9
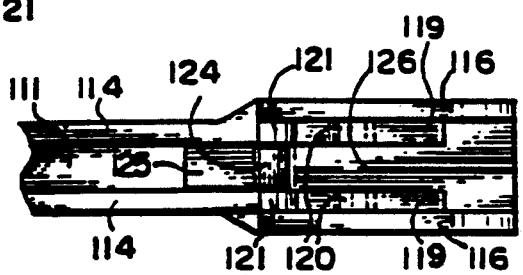
FIG. 9A
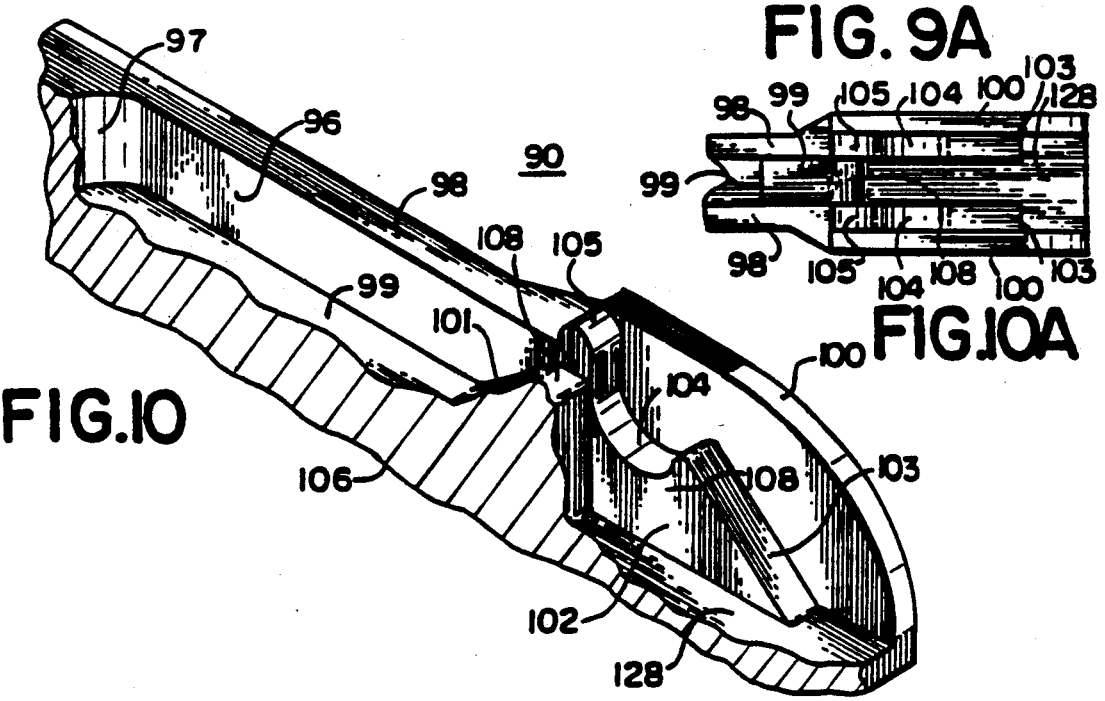
FIG. 10
FIG. 10A

LIGATING CLIP APPLYING INSTRUMENT

This is a divisional application of application Ser. No. 07/422,464 filed Oct. 17, 1989, now U.S. Pat. No. 5,062,846, which is a continuation-in-part of application Ser. No. 329,453, filed Mar. 28, 1989, now abandoned, which was a divisional of application Ser. No. 206,143, filed Jun. 13, 1988, now U.S. Pat. No. 4,834,096, issued May 30, 1989, which was a continuation-in-part of application Ser. No. 112,599, filed Oct. 26, 1987, now abandoned.

BACKGROUND OF THE INVENTION

The present invention relates to surgical clips and clip appliers and more particularly to penetrating polymeric hemostatic clips and instruments for applying them.

Surgical clips like hemostatic clips and aneurysm clips are often used in surgery to ligate vessels to stop the flow of blood. Surgical clips are also used to interrupt or occlude the oviduct or vas deferens in sterilization procedures. The clips are left in place permanently and within a period of time the ligated end of the vessel will close, that is, hemostasis or occlusion will occur.

Metal clips having generally U or V shapes have been used for years. The most common metals are alloys of tantalum, titanium or stainless steel, all of which are deformed into a closed position about the vessel and because of the nature of the metal stay deformed and resist any force by the vessel to expand or open up.

Metal clips cause a certain amount of interference with high technology diagnostic modalities, including Computer Tomography (CATSCAN) and Magnetic Resonance Imaging (MRI). In particular, the new and emerging MRI techniques place stringent demands on the non-interference properties of clips. For example, existing fast imaging techniques for MRI give rise to at least one order of magnitude in increased sensitivity to magnetic field inhomogenieties brought about by metallic clips. Field uniformities of one in $10^5$ are required but metal clips, particularly stainless steel clips, can reduce the homogeniety in the locality of the clip to the order of $10^4$ or less.

To aggravate the situation even more recent developments in in vivo Magnetic Resonance Spectroscopy (MRS) create even greater demands on minimizing magnetic field interferences (field uniformities approximately one in $10^7$ required). Existing metal clips preclude the use of MRS data taken in the proximity of the metal clips. This region is as large as six clip diameters for titanium and tantalum and more than fifty clip diameters for stainless steel.

To overcome the above problems, in recent years plastic clips have been introduced. These clips generally should be as small as possible, e.g., as small as their metal counterparts. Plastic clips require a latching means to keep the clip closed once they are clamped about the vessel since, unlike metal clips, they have insufficient resistance to the forces tending to open the vessels. The requirement to latch presents an additional problem since the polymeric clip must surround the vessel to do so. Therefore, the vessel to be ligated must not be attached to any surrounding tissue. Without more, such clips would require that the surgeon dissect the vessels from the surrounding connective tissue and this would be very time consuming. With metal clips this is not necessary since metal clips need not surround the vessel to occlude it. It is desirable, therefore, to provide a polymeric clip capable of occluding a vessel attached to connective tissue.

Most of the new plastic clips now in the market are made of a biodegradable and absorbable polymeric material. Generally, the absorbable clips, owing to their comparatively high water sorption do not reflect the mechanical strength levels which are available from modern engineering plastics and therefore represent a size increase compromise in order to provide comparative strength. The use of high performance polymer materials permits increased design options for functional improvements.

It is, therefore, desirable to produce a small, but secure, biocompatible and strong polymeric surgical clip which may be used to close vessels connected to surrounding tissue.

SUMMARY OF THE INVENTION

The surgical clip of the present invention is made of polymeric material and accordingly minimizes interference with high technology diagnostic modalities such as CATSCAN, MRI and MRS. At the same time, the clip is nearly as small as comparable metal clips, while maintaining sufficient strength and possessing high security in the clip's latching mechanism in the closed position clamping the vessel. The clip is configured to provide a secure means of handling and application to avoid premature release from the applier, and includes means for penetrating through surrounding tissue connected to the vessel.

A surgical clip is provided which comprises first and second curved leg members joined at their proximal ends by a hinge means and disposed to be latched together in the closed position at their distal ends. The leg members each include complementary curved, opposing inner surfaces, the inner surface of the first leg being concave in shape. The first leg member further includes a hook portion joined at its distal end and curved toward said second leg member. The hook portion includes a continuously curved outer surface extending from the outer surface of the distal end of the first leg and a distal tip portion forming a sharp pointed distal tip extending rearwardly toward the proximal end of the first leg. The hook portion may also include a sharp pointed member attached to the outer surface of the distal tip portion.

The hook portion is disposed to engage the outer surface of the distal end of the second leg member when the clip is in the closed position. The distal end of the second leg member includes a groove through which the the sharp pointed distal tip presses when the first and second leg members are moved from the open position to a closed position. Where the clip includes a sharp pointed member the sharp pointed member passes through the groove ahead of the sharp pointed distal tip. The sharp pointed member engages, stretches and penetrates connective tissue connected to the vessel to be clamped. In the stretched position, the connective tissue is more easily penetrated and cut by the sharp distal tip as the clip is closed.

To assist in cutting the connective tissue to allow the clip leg members to latch, sharp penetrating members are attached on either side of the distal end of the second leg member on either side of the groove. Each member has a sharp distal tip which extends beyond the inner surface of the second leg member. Preferably, the radius of curvature of the distal tips of the distal tip portion of the first leg and the sharp pointed members of the second leg are less then 0.002 inches in their principal planes.

The outer surface of the second leg member opposite the inner convex surface is concave in shape. This configuration provides a more secure latching mechanism, since any forces by the clamped vessel tending to open the clip will force the second leg to lengthen and the first leg member to shorten moving the distal end of the second leg member into further engagement with the hook portion. Because the thickness of the second leg member is smaller than it would have been without the concave outer surface, the second leg member will deflect upon clamping or in response to the forces exerted on it by the clamped vessel and because the thickness of each leg between its inner and opposite outer surfaces between the hinge and distal end is substantially equal to the thickness of the other leg, the total deflection necessary to accommodate closing and clamping of the vessel is distributed between the two legs helping to avoid breakage or failure of either leg. In the preferred embodiment, the radius of curvature of the inner concave surface of the first leg member is the same as the radius of curvature of the inner convex surface of the second leg member. This provides a constant compressive force across the entire width of the vessel being clamped.

The inner and outer surfaces of the hook portion are substantially continuously curved to prevent excessive stress concentration occurring at corners or small radius points in the hook portion.

The clip further comprises means for allowing the clip to be engaged by a suitable forceps type applier comprising at least a pair of bosses located on the sides of the first leg member intermediate the hinge means and the hook portion and a pair of bosses also located on the sides of the second leg member at the distal end. The sharp pointed members extend from these bosses. The bosses are so disposed as to extend beyond the end of the second leg member to provide two parallel and separately spaced surfaces which prevent lateral movement of the leg members relative to one another when the clip is closed. The bosses are used by the applier in holding and applying the clip.

The clip of the present invention may also include a plurality of protrusions on the inner surfaces of the leg members to aid in retention of the clamped vessel. The protrusions may be ratchet type, wedge shaped, to provide one way vascular movement into, but not out of, the clip.

A ligating clip applying instrument for applying two legged ligating clips having means for engaging the bosses located on the sides of the legs is also provided. The jaws of the instrument include a channel to receive the clip and a concave cut out near the end of each jaw. Each wall may also include an arcuate wall portion adjacent to and on the outside of the cut out.

The instrument further comprises a protrusion in the floor of each of said channels which is directed toward the opposite jaw, the protrusion being located proximally of the concave cut outs. Each protrusion engages a leg of the clip to assist in forcing the legs toward one another as the jaws are closed.

BRIEF DESCRIPTION OF THE DRAWINGS

FIG. 8 illustrates an enlarged planar elevational view of a forceps type applier useful with the clip of the present invention.

FIG. 9 is a greatly enlarged perspective view of a break away of a first jaw of the applier of FIG. 8.

FIG. 9A is a bottom planar view of the first jaw of FIG. 9.

FIG. 10 is a greatly enlarged perspective view of a break away of a second jaw of the applier of FIG. 8.

FIG. 10A is a bottom planar view of the second jaw of FIG. 10.

DETAILED DESCRIPTION OF THE DRAWINGS

Figure 1:
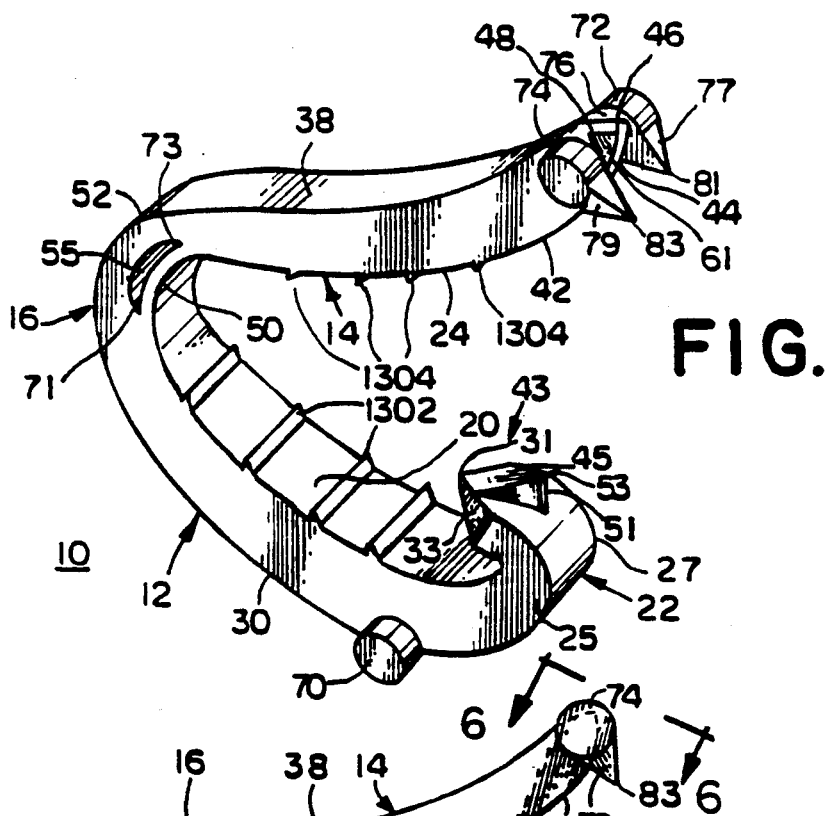
FIG. 1 is an enlarged perspective view of the surgical clip of the present invention.
Figure 2:
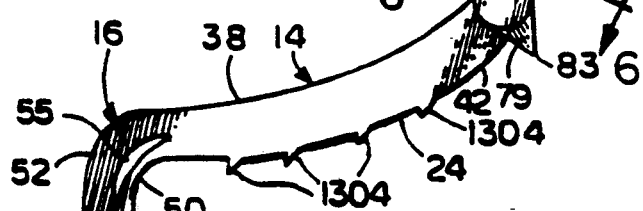
FIG. 2 is a side elevational view of the clip of FIG. 1.

Referring now to FIGS. 1-6, a preferred embodiment surgical clip designated generally 10 is shown. It comprises a first curved leg member 12 and a second curved leg member 14 joined at their proximal ends by a hinge portion 16.. First leg member 12 has a concave inner surface 20 and a curved hook portion 22 joined at its distal end. The inner surface 24 of second curved leg member 14 is convex and is adapted to be substantially parallel with concave inner surface 20 when the clip is closed, i.e.; the radius of curvature of the concave inner surface 20 is substantially the same as the radius of curvature of the inner convex surface 24. The hook portion 22 is curved toward the distal end of second leg member 14.

The hook portion 22 comprises a continuously curved outer surface 28 which continues from the convex outer surface 30 of the first leg member with decreasing radius of curvature. The inner surface of the first curved section is continuously curved and continues from the inner concave surface 20 of the first leg member 12 in a decreasing radius of curvature to a constant terminal radius of curvature. The first leg member 12 further comprises generally flat parallel side surfaces 25 and 27 which extend between the inner and outer surfaces of the first leg member and the the hook portion 22. In the preferred embodiment the thickness of the first leg member between its inner and outer surfaces 20 and 30, respectively, and most of the hook portion between its inner and outer surface 26 and 28, respectively, remains generally constant throughout its length.

Figure 4:
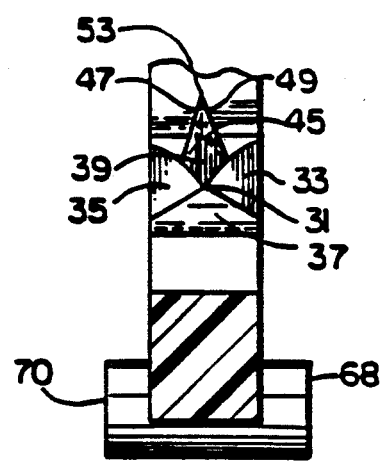
FIG. 4 is a cross-sectional view of the clip of FIG. 2 taken along the lines and arrows 4—4 in FIG. 2.

The hook portion 22 terminates in a distal tip portion 29 which extends rearwardly and itself terminates in a sharp pointed distal tip 31 which points generally toward the proximal end of the clip 10. As best seen in FIG. 4, the sharp tip 31 is formed by inwardly tapered surfaces odd numbers 33 through 39. Surfaces 33 and 35 converge and narrow to the tip 31 from side surfaces 25 and 27, respectively; surface 37 converges and narrows from a flat surface 41 which extends to the terminal radius of curvature portion of inner surface 26; and surface 39 converges from the curved surface 28 of the hook portion. To enhance the penetration effect, the radius of curvature of the tip in the center plane of the clip and in a plane orthogonal thereto should be less then 0.002 inches. This compares favorably with the sharpness of a skin staple tip.

The distal tip portion 29 of the first leg member further includes a sharp pointed member 43 attached to the outer surface of the portion 29. The member 43 is formed from a sloped surface 45 which extends away from the curved outer surface of the distal tip portion and the sharp tip 31, somewhat in a direction away from the hinge portion of the clip. It comprises sloped sides 47 and 49 (see FIGS. 4 and 5) and an edge 51 which returns to the curved outer surface of the hook portion 22. The exterior tip 53 of the sharp pointed member 43 has a radius of curvature of approximately 0.002 inches.

Figure 3:
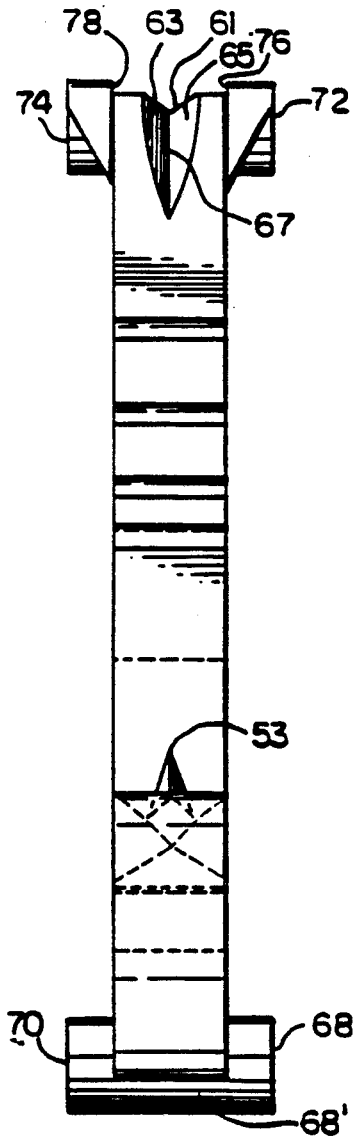
FIG. 3 is a front elevational view of the clip of FIG. 2 looking into the open end of the clip.
Figure 6:
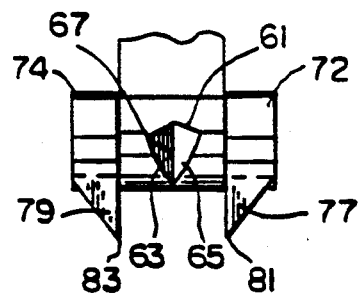
FIG. 6 is an end view of the distal end of another leg portion of FIG. 2 taken along the lines and arrows 6—6 in FIG. 2.
Figure 5:
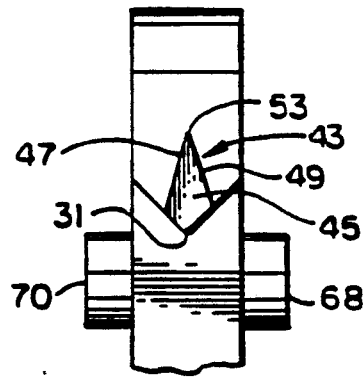
FIG. 5 is a top view of the distal end of a leg portion of FIG. 2 taken along the lines and arrows 5—5 in FIG. 2.

The second leg member 14 has a banana like profile along its length between its inner convex surface 24 and outer concave surface 38. The thickness of the distal end has a rapid reduction in thickness because of the change in radius of curvature of its inner surface 24 at 42 to form a curved inner beveled surface 44 terminating in a curved tip 46 and the relatively flat beveled surface 48 joining the outer concave surface 38 to the tip 46. The distal end of the second leg includes a groove 61 in the center plane of the clip which passes through the tip 46. As best seen in FIGS. 3 and 6 the groove 61 is formed by inwardly directed tapered side walls 63 and 65 cut into the distal end of the second leg member. The bottom of the groove is represented by line 67.

The thickness of the second leg member 14 between its inner and outer surfaces 24 and 38, respectively, between the hinge portion 16 and its distal end may vary by ten to twenty percent with the leg being thickest at its center region. Generally the thickness of the second leg 14 is substantially the same as the thickness of the first leg 12 except for this variation in the center where the second leg may be slightly thicker. The thickness of the first leg 12 could be increased, however, in the center region to match the thickness of the first leg by varying the outer convex surface 30 of the first leg 12 but the radius of curvature of the concave inner surface 20 remains equal to the radius of curvature of the convex inner surface 24 of the second leg member 14. The thickness of the second leg member 14 being slightly thicker in the center causes the first leg member to deflect a little more than the second leg member when the clip is being clamped about a vessel, but the second leg member is disposed because of its outer concave surface to deflect substantially during closure so that total defection of the legs necessary to clamp a vessel and latch the clip is being shared about equally by the legs.

Hinge portion 16 comprises an inner continuously curved concave surface 50 which joins the inner concave and convex surfaces 20 and 24, respectively, and an outer continuously curved surface 52 which joins outer convex and concave surfaces 30 and 38, respectively, and which is spaced apart from inner hinge concave surface 50. The hinge portion 16 further includes a curved slot 55 which is located between curved hinge surfaces 50 and 52, being positioned closer to concave hinge surface 50 than to convex hinge surface 52. The slot extends completely through the hinge portion 16 from side to side and its opposite ends 71 and 73 extend into the proximal ends of the leg members 12 and 14, respectively. The slot 53 provides added flexibility to the hinge 16 but the inner concave surface 50 prevents any portion of the clamped vessel from being trapped within the slot 53.

Leg member 12 includes a pair of cylindrical bosses 68 and 70 coupled on opposite sides of leg member 12 intermediate the hook portion 22 and the hinge portion 16, but closer to the hook portion 22 in the preferred embodiment. The bosses extend laterally away from the leg member beyond the outer surface 30 of the leg member 12. The bosses are coupled to one another across the width of leg member where they extend beyond the outer surface 30 for a cylindrical portion 68'.

Leg member 14 includes a pair of cylindrical bosses 72 and 74 located at the tip 46 on opposite sides of the leg member 14 and extending laterally away therefrom. In the preferred embodiment, the coaxial center line of the bosses 72 and 74 passes through the tip portion of the leg member 14. The bosses 72 and 74 extend beyond the tip leaving spaced apart opposing surfaces 76 and 78, respectively.

The second leg member further includes a pair of sharp penetrating members 77 and 79 extending from the bosses 72 and 74, respectively, past the inner surface 24 of the leg 14. The sharp penetrating members are located on either side of the groove 61 and terminate in sharp point 81 and 83, respectively. The sharp points 81 and 83 are in a plane with the plane of the interior boss surfaces 76 and 78, respectively (see FIG. 3). The tips have a radius of curvature in that plane of approximately 0.002 inches.

FIG. 8 shows a forceps type clip applier 80 which includes two handles 82 and 84 coupled together and crossing at a hinge 86. The handles are biased into an open position by the spring 88. The handles 82 and 84 extend beyond the hinge 86 to form jaws 90 and 92, respectively.

FIG. 9 is an enlarged break away of a portion of the jaw 90 while FIG. 9A is a planar view of the jaw 90 of FIG. 9 both showing the details of its construction. The jaw 90 includes a channel 96 which extends from a position 97 rearward of the tip of the jaw towards the tip. The thickness of the outside walls 98 of the channel widen as they approach the end of the jaw to form arcuate outside walls 100 of the end of the jaw and inward adjacent walls 102 with rearwardly directed sloped surfaces 103 and concave cut outs 104. The inner surfaces of the walls 102 are contiguous with and in the same plane as the inner surfaces of the walls 98 which form the channel 96. Where the walls 98 widen to form the outside arcuate walls 100 and adjacent walls 102, the cut outs 104 extend beyond the top surfaces of the walls 98 toward the opposite jaw to form rounded shoulders 105. The adjacent arcuate walls 100 also are raised above the top surfaces of walls 98 by the same amount.

The floor 99 of channel 96 is spaced apart and parallel with the top surfaces of walls 98 of the jaw along a portion extending from the rearward terminus 97 of the channel until the floor extends towards the opposite jaw along ramp 101 to form a protrusion 108 located just as the cut outs 104 extend above the top surfaces of walls 98. The protrusion 108 drops straight off to a flat portion 128 of the jaw which flat portion extends to the tip. The jaw has a flat outer bottom surface 106.

FIG. 10 is an enlarged break away of a portion of jaw 92 while FIG. 10A is a planar view of the jaw 92 of FIG. 10 both showing the details of its construction, which are identical to the construction of jaw 90. The jaw includes a channel 110 which extends from a position 112 rearward of the tip of the jaw toward the tip. The outside walls 114 of the channel widen as they approach the end of the jaw to form arcuate outside walls 116 of the end of the jaw and inward adjacent walls 118 with rearwardly directed sloped surfaces 119 and concave cut outs 120. The inner surfaces of the walls 118 are contiguous with and in the same plane as the inner surfaces of the walls 114 which form the channel 110. Where the walls 114 widen to form walls 116 and 118, the cut outs 120 extend towards the opposite jaw beyond the top surfaces of walls 114 to form rounded shoulders 121. The arcuate walls 116 extend beyond the top surface by the same amount. The floor 111 of channel 110 is spaced apart and parallel with the top surface of walls 114 of the jaw along a portion extending from the rearward terminus 112 of the channel until the floor extends towards the opposite jaw along ramp 125 to form a protrusion 124 located just as the cut outs 121 extend above the top surfaces of walls 114. The protrusion 124 drops straight off to the bottom of the jaw which extends to the tip. The jaw has a flat outer bottom surface 122.

Figures 11A, 11B:
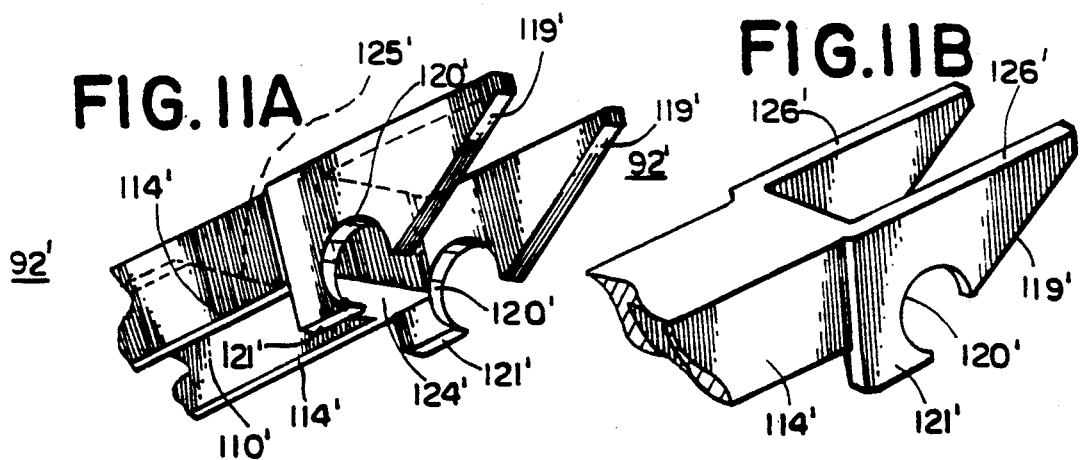
FIG. 11A and 11B are greatly enlarged perspective views of an alternate embodiment of the jaw portion of the applier of FIG. 8.

FIGS. 11A and 11B show an alternate embodiment of the jaw of the clip applier of FIGS. 8 through 10A. Like parts are labelled with a prime'. The clip applier includes two handles like handles 82 and 84 coupled together and crossing at a hinge 86 (not shown in FIGS. 11A and 11B). The handles are biased into an open position by a spring, like spring 88 in FIG. 8. The handles extend beyond the hinge to form identical opposing jaws. Jaw 92' is shown by way of example. The lower jaw is identical. Referring to FIG. 11A, the jaw 92' includes a channel 110 which extends from a position rearward of the tip of the jaw toward the tip. The channel is formed by outside walls 114' which have distal portions with rearwardly directed sloped surfaces 119' and concave cut outs 120'. Just behind the cut outs 120', the walls 114' extend toward the opposite jaw to form shoulders 121' which protrude above the top surfaces of the walls 114' which are proximal of the shoulder. The floor (not shown) of channel 110' is spaced apart and parallel with the top surfaces of the proximal portions of walls 114' along a portion extending from the rearward terminus of the channel until the floor extends towards the opposite jaw along ramp 125' to form a protrusion 124' located just as the shoulder's 121' extend above the top surfaces of walls 114'. The protrusion 124' drops straight off to the bottom of the jaw. The cut outs 120' are formed in wall portions of the distal portion of the jaws which are parallel and spaced apart from one another and are unconnected along their bottom edges 126'.

FIGS. 12A through 12E show how the applier of FIGS. 11A and 11B is used in applying the clip 10. The applier of FIGS. 8–10A would work as well. The clip 10 is in the open position with the general axes of the leg members 12 and 14 forming an acute angle at the hinge, but the clip could be open as much as 90° or more. The jaws of the applier 92' are biased open by an amount equal to the opening of the clip. As the applier is moved in the direction of arrow 1200 in FIG. 12A, the bosses 72, 74 and 68, 70 (only bosses 68 and 72 are shown) are forced to ride up the rearwardly directed inclined surfaces 119' of the distal portions of the walls forcing the clip to close slightly until the bosses seat in cut outs 120' as in FIG. 12B.

The cut outs of each jaw are spaced apart from one another by the channel of each jaw which is at least as wide as the width of the clip and the cut outs are disposed to receive the bosses. The concave cut outs keep the clips aligned and locked within the jaws, during the closing. The concave cut outs 120' press against the bosses to begin closure of the clip.

Figures 12A, 12B:
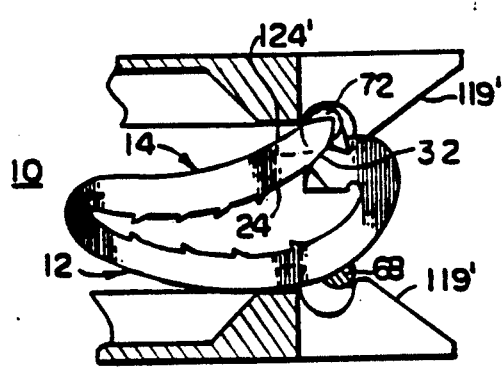
FIGS. 12A to 12E illustrate the use of the applier of FIGS. 11A and 11B in applying the clip of the present invention.
Figures 12C, 12D:
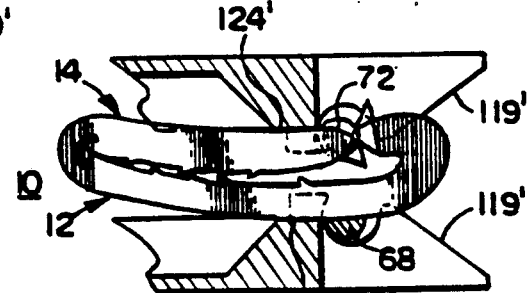
Figure 12E:
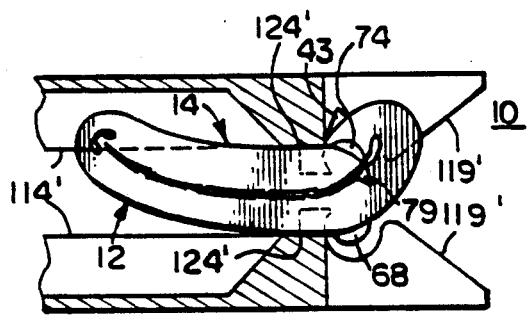

After the boss pairs 72, 74 and 68, 70 seat themselves in the concave cut outs, the raised shoulders 124' of jaws 92', respectively, press against the outside surfaces of leg members 12 and 14 to continue closure of the clip 10 (see FIGS. 12B–12E). Eventually the outside surface 32 of the hook portion 22 engages the inner surface 24 of leg member 14 near the curved bevel surface 44. See FIG. 12C. As the leg members continue to be pressed together, the rounded outside surface of the hook portion 22 slides along the curved bevel surface 44 and around tip 46 (FIG. 12D) until the flat surface 41 on the end of the hook portion 22 engages the flat beveled surface 48 on the outside of the leg member 14 closing the clip (FIG. 12E). The channels 110' accommodate the body of the clip within the jaws during the closing process. As best seen in FIG. 12D, both leg members deflect under the forces exerted on the clip during closure to accommodate movement of the hook portion of leg member 12 around the tip of leg member 14.

Figure 13A:
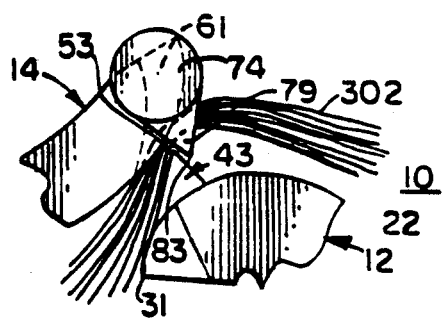
FIGS. 13A through 13E show in enlarged detail the hook portion of one leg member and the distal end of the other leg member in various progressive stages of closure penetrating connective tissue attached to the vessel being clamped.

The overall mechanics of clip closure were discussed in connection with FIGS. 12A through 12E. Referring now to FIGS. 13A through 13E, the functioning of the sharp penetrating members 43, 77 and 79, the groove 61 and the sharp distal tip 31 will be described. The connective tissue 302 is shown in each of the FIGS. 13A through 13E in between the distal end of leg member 14 and the hook portion 22 as the clip is closed. In FIG. 13A, before any contact is made between the leg members, the sharp points 81 and 83 of the spaced apart penetrating members 77 and 79 of the second leg start to indent and penetrate the tissue 302 and pull tissue down, while in between the members 77 and 79, the sharp point 53 of penetrating member 43 begins to penetrate the tissue and force the tissue up.

Figure 13B:
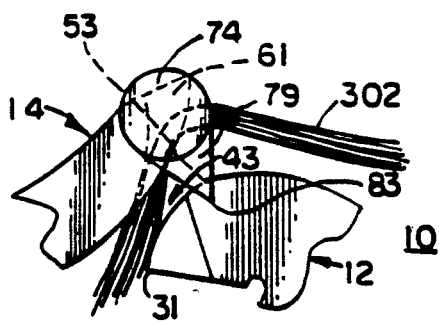
Figure 13C:
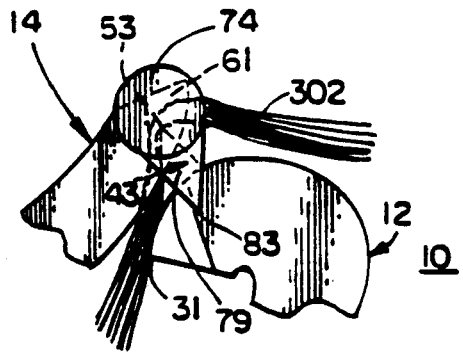

In FIG. 13B, the tip 53 enters the groove 61 on the second leg member and puncturing of the tissue begins. In FIG. 13C, the penetrating member 43 is moving through groove 61 and as penetrating members 77 and 79 move closely alongside the sides of the hook portion of the leg 12, shear forces contribute to puncturing of the tissue by the tips 81 and 83. After puncture, the knife-like edges of the penetrating member 77 and 79 help to tear the tissue 302 as the leg 14 moves down. There is still little or no contact between the penetrating member 43 and the groove 61. The tissue caught between the distal end of the second leg and hook portion 22 begins to stretch. Tissue is jammed between three sharp edges which move in opposite directions.

Figure 13D:
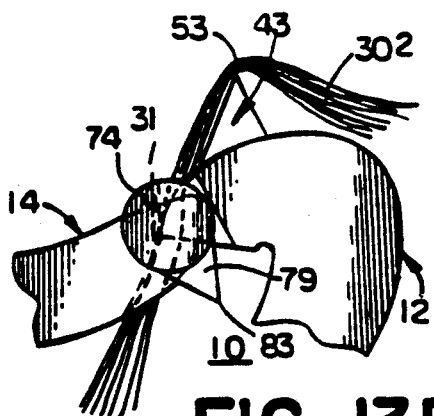
Figure 13E:
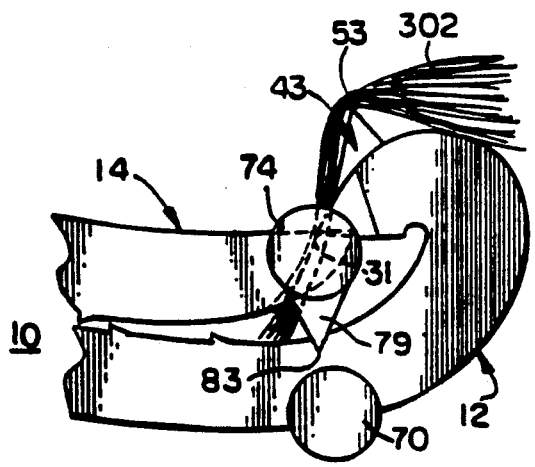

In FIG. 13D, if the tissue is not yet cut between the distal portion of the second leg member and the hook portion it will be stretched and become thinner and more easily punctured by the sharp point 31 of the distal portion of the hook portion 22 as it passes through the groove 61 and flat beveled surface 48. This point is quite sharp (less than 0.002 inches) and cuts to remaining stretched tissue. The tissue which is very elastomeric is made more penetrable by stretching. In FIG. 13E the final stage of cutting and stretching is shown. If all the tissue is not cut, what remains will be quite thin, allowing the clip to latch.

Figure 7:
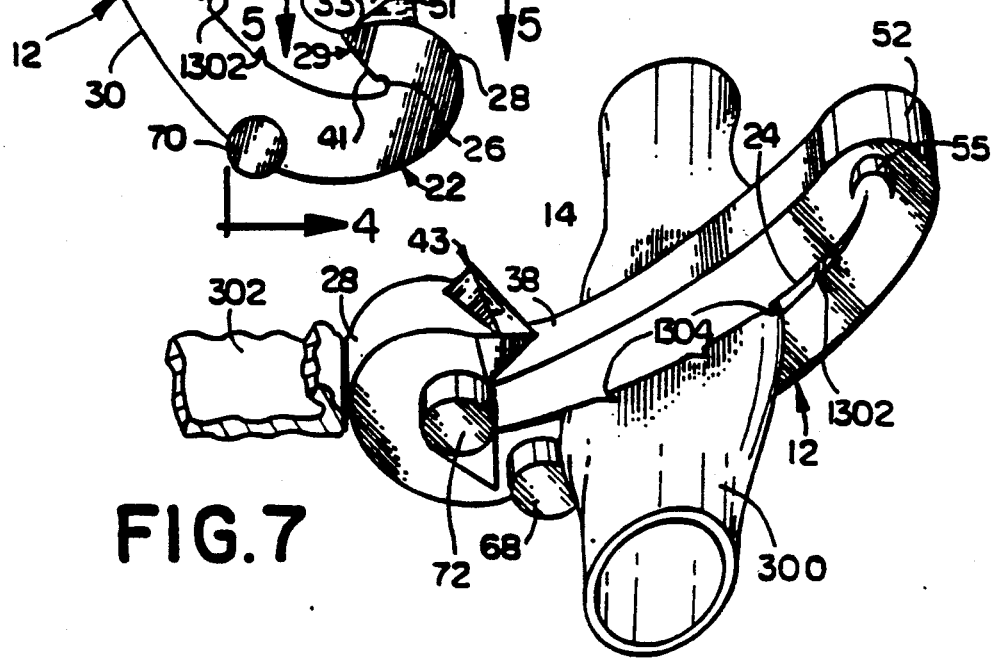
FIG. 7 shows the clip of FIG. 1 applied to a body vessel.

FIG. 7 shows the clip closed about a vessel 300 which has been separated from connective tissue 302 at least in the area of the clip. In the preferred embodiment the radius of curvature of the inner convex surface of second leg member 14 is substantially the same as the radius of curvature of the inner concave surface of first leg member 12. This causes a relatively even distribution across the width of the clamped vessel of the compressive forces being exerted by the clip leg members 12 and 14. The vessel 300, particularly if large or upon swelling, will exert a counter force against the legs of the clip after application tending to open up the clip. The outer concave surface reduces the thickness of the second leg member such that it will deflect and lengthen in response to forces by the clamped vessel tending to open the clip. Lengthening of the second leg member moves the distal end of the second leg member farther into the hook portion. At the same time, the forces by the clamped vessel exerted on the first leg member will tend to shorten the first leg member moving the hook portion closer to the hinge and the distal end of the second leg member. This configuration provides for a more secure latching. Also, because the thickness of the second leg member is smaller than it would have been without the concave outer surface, and is substantially the same as the first leg member between its inner and opposite outer surface, the total deflection necessary to accommodate closing and clamping of the vessel is distributed between the two legs with a substantial amount of deflection being taken up by second leg member helping to enhance the security of the latching effect and avoid premature failure of either leg. The thickness of the second leg member in the center region is slightly larger than the thickness of the first leg member or corresponding center region in order that the second leg member will bend slightly less than the first leg member to avoid passing the flattening position from which unlatching is facilitated. Both leg members can be made with equal thickness, however.

The inner surfaces of the side bosses 72 and 74 which extend beyond the tip 46 of the leg member 74 prevent the hook member 22 and leg member 14 from moving laterally relative to one another, once the clip is closed.

By providing a continuous relatively large radii of curvature to both the inner and outer surfaces of the hinge portion and the hook portion, sharp interior corners which create unwanted stress concentration, which can lead to clip failure, are eliminated.

Referring once again to FIG. 1 and 2, the clip 10 of FIG. 1 further includes a plurality of protrusions 1302 on the inner surface 20 of the leg member 12, while leg member 14 includes a plurality of protrusions 1304 on its inner surface 24. The protrusions are wedge shaped with the wedge opening up towards the hinge portion. The protrusions engage the tissue of the vessel being clamped and assist in preventing the vessel sliding laterally or longitudinally during or following clip closure. It is preferable that the clip clamp the vessel substantially across the vessel at 90° to the axis of the vessel. The vessel being dynamic may move or pulse and such movement may cause the clip to become misaligned degrading its performance or function. The protrusions help in preventing this.

Figure 14:
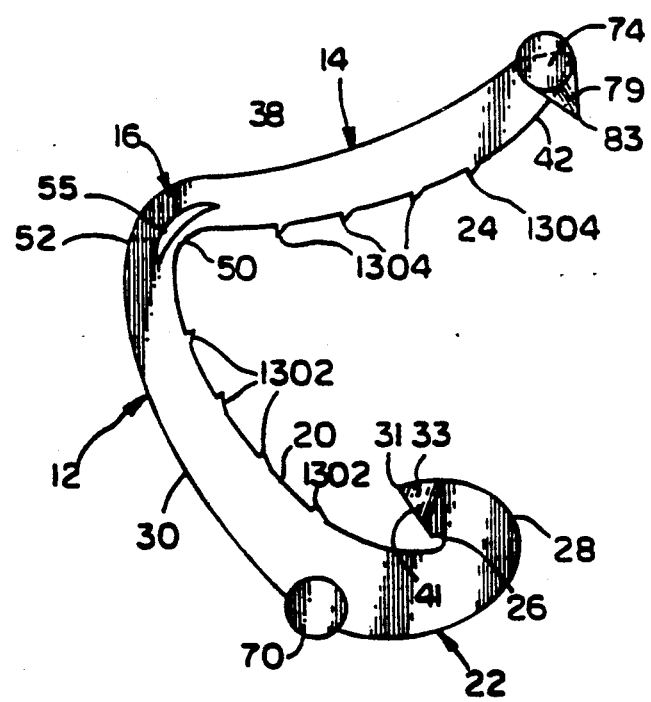
FIG. 14 is a side elevational view of an alternate embodiment of the clip of FIG. 1.

FIG. 14 shows a side elevations view of the clip of FIG. 1 without the sharp penetrating member 43. Like parts are numbered the same in FIG. 14 as in FIG. 2. While the sharp penetrating member adds to the penetration of the connective tissue, particularly in stretching the tissue which makes it more susceptible to cutting by the sharp distal tip 31, it is believed that the member 43 is not absolutely necessary and that the clip will act satisfactorily without the member 43. One advantage to the embodiment of FIG. 14 is that there are NO protruding sharp members present beyond the profile of the closed clip after the clip has be clamped about a vessel. This avoids possible damage to surrounding tissue by the protruding member 43.

The clip of FIGS. 1-14 is preferably a single integral piece of molded plastic. The plastic material chosen is preferably one of the many relatively strong engineering plastics available today which are commonly used in surgical implant operations and are biocompatible. Two examples of suitable plastics are polyethylene terephthalate (PET) and polyoxymethylene. These are both thermoplastic materials that can be injection molded, extruded or otherwise thermally processed into shaped articles and filaments. An alternate, molding grade polyester, polybutylene terephthalate (PBT) can also be used.

As mentioned earlier it is preferable that any plastic surgical clip, such as a hemostatic clip, be as small as its metal equivalent. The preferred embodiment clip can be made as small as seven millimeters in overall length in the closed position as measured from the back of the hinge to the outside of the hook portion. This is to be compared with a medium size metal hemostatic clip which is approximately six millimeters in length when closed. Each leg of the polymeric clip of the present invention has a maximum thickness in the order of 1.0 millimeters or less with a weight of about 0.015 grams, a volume of 0.01 cubic centimeters and an opening of 4 millimeters or more.

In the preferred embodiment, the radius of curvature of the inner surface of the leg 12 starts out as 0.166 inches near the peninsular portion 56, changes to 0.222 inches at the center region up to the hook portion 22 where it changes to 0.052 inches and then to 0.007 inches. The outer surface of the hook portion starting at its end 32 is 0.045 inches then 0.036 inches. As the hook portion ends and the outer surface 30 of leg member 12 continues towards the hinge the radius of curvature changes from 0.108 inches, to 0.246 inches, to 0.171 inches near the hinge 16. The hinge's outer surface 52 has a radius of 0.042 inches until the outer concave surface 38 of the leg member 14 begins at the radius of 0.161 inches and then 0.231 inches near the tip 46 (radius of 0.003 inches). The radius of the curved beveled surface 44 is 0.044 inches up until the start of the convex inner surface 24 of leg member 14 which is 0.222 inches and then 0.166 inches. The radii are provided to give an example of the degree of curvature of the clip and to show that the curved surfaces are generally continuous. The centers of the radii, even for the concave and convex surfaces, such as, the inner and outer surfaces of the leg members, are not generally the same. While these radii reflect the radii for the preferred embodiment clip, it should be understood that variations or changes from these radii are encompassed by the present invention curved clip.

While the embodiments of the surgical clip described herein above are particularly adapted for hemostatic application, they may also have other applications, e.g. as oviduct or vas deferens clips.

What is claimed is:

1. A ligating clip applying instrument for applying two legged ligating clips having engagement means on the lateral sides of said legs comprising: a pair of handles pivoted about a hinge point and extending beyond the hinge point to form a pair of clip closing jaws having opposing inner faces, each of said jaws having a recessed clip receiving channel in the inner face thereof extending from the tip of said jaw rearward toward said hinge point, said channel having a length at least equal to the length of the clip to be applied by the instrument; and each of said jaws comprising means for engaging said clip engagement means, said means for engagement comprising each wall on either said of said channel in each jaw comprising a concave cut out near the end of said jaw and an arcuate wall portion adjacent to an on the outside of said cut out.

2. The instrument of claim 1 wherein the back wall of each concave cut out protrudes away from the channel in the direction of said opposing jaw.

3. The instrument of claim 2 wherein the height of said adjoining arcuate wall portion is substantially equal to the height of said protruding back wall.

4. The instrument of claim 2 wherein the bottom of the channel in each of said jaws forms a protrusion directed toward said opposed jaw between the portions of said cut outs which protrude toward said opposite jaw.

5. A ligating clip applying instrument for applying two legged ligating clips having engagement means on the lateral sides of said legs comprising: a pair of handles pivoted about a hinge point and extending beyond the hinge point to form a pair of clip closing jaws having opposing inner faces, each of said jaws having a predetermined width and a clip receiving space in its inner face extending from the tip of said jaw rearward toward said hinge point, and each of said jaws provided with clip engagement means on its inner face, said clip engagement means comprising a pair of spaced walls, each wall having a concave cut out facing the opposing wall.

6. A ligating clip applying instrument comprising: a pair of handles pivoted about a hinge pivot and extending beyond the hinge point to form a pair of clip closing jaws having opposing inner faces, each of said jaws having a pair of spaced walls adjacent the distal end thereof, each of said walls being inwardly directed toward the opposite jaw and having a recess for receiving an engagement means affixed to the lateral side of a ligating clip.

7. A clip applying instrument according to claim 6 wherein said instrument is adapted for use with a clip having a projection adjacent and on each lateral side of the end of each clip leg and wherein said recesses of said walls are adapted to receive said projections.

* * * * *

UNITED STATES PATENT AND TRADEMARK OFFICE
CERTIFICATE OF CORRECTION

PATENT NO. : 5,100,416
DATED : MARCH 31, 1992
INVENTOR(S) : SEIK OH

It is certified that error appears in the above-identified patent and that said Letters Patent is hereby corrected as shown below:

On the title page, item [75]:
    Please change the inventors named from "Seik Oh and Ray McKinney, Jr." to
-- Seik Oh --

Signed and Sealed this

First Day of March, 1994

Attest:

BRUCE LEHMAN

Attesting Officer     Commissioner of Patents and Trademarks